US011033687B2

(12) United States Patent
Nessel et al.

(10) Patent No.: US 11,033,687 B2
(45) Date of Patent: Jun. 15, 2021

(54) INJECTION DEVICE FOR DELIVERY OF A LIQUID MEDICAMENT

(71) Applicant: SANOFI-AVENTIS DEUTSCHLAND GMBH, Frankfurt am Main (DE)

(72) Inventors: Christian Nessel, Frankfurt am Main (DE); Christian Dexheimer, Rüsselsheim (DE); Florian Hammen, Rüsselsheim (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 156 days.

(21) Appl. No.: 15/572,902

(22) PCT Filed: May 13, 2016

(86) PCT No.: PCT/EP2016/060855
§ 371 (c)(1),
(2) Date: Nov. 9, 2017

(87) PCT Pub. No.: WO2016/180967
PCT Pub. Date: Nov. 17, 2016

(65) Prior Publication Data
US 2018/0104417 A1 Apr. 19, 2018

(30) Foreign Application Priority Data
May 13, 2015 (EP) .................................. 15167539

(51) Int. Cl.
*A61M 5/20* (2006.01)
*A61M 5/145* (2006.01)
(Continued)

(52) U.S. Cl.
CPC ........ *A61M 5/2053* (2013.01); *A61M 5/1454* (2013.01); *A61M 5/14526* (2013.01);
(Continued)

(58) Field of Classification Search
CPC ............ A61M 5/2053; A61M 5/14526; A61M 5/14566; A61M 5/48; A61M 5/145
See application file for complete search history.

(56) References Cited

U.S. PATENT DOCUMENTS 4,451,255 A * 5/1984 Bujan ............... A61M 5/16827
604/151
2002/0123718 A1* 9/2002 Landau .................... A61M 5/30
604/70
(Continued)

FOREIGN PATENT DOCUMENTS

CN 1585655 2/2005
CN 1694739 11/2005
(Continued)

OTHER PUBLICATIONS

International Search Report and Written Opinion in International Application No. PCT/EP2016/060855, dated Aug. 12, 2016, 8 pages.
(Continued)

Primary Examiner — Nathan R Price
Assistant Examiner — Dung T Ulsh
(74) Attorney, Agent, or Firm — Fish & Richardson P.C.

(57) ABSTRACT

An injection device for dispensing of a liquid medicament is disclosed. The device includes an elongated housing extending in an axial direction to accommodate a cartridge, a drive member axially displaceable inside the housing and being in sealed engagement with a side wall of the housing, wherein the drive member has an abutment face to axially abut with a proximal end of a barrel of the cartridge to displace the cartridge from the undeployed position towards the deployed position, wherein the drive member has an outlet located distally from the sealed engagement and further has an inlet located proximally from the sealed engagement, wherein the inlet and the outlet are in flow connection with
(Continued)

each other via a flow path extending through the drive member and wherein at least one flow restrictor is arranged across or in the flow path.

17 Claims, 6 Drawing Sheets

(51) Int. Cl.
*A61M 5/48* (2006.01)
*A61M 5/315* (2006.01)

(52) U.S. Cl.
CPC ......... *A61M 5/482* (2013.01); *A61M 5/14566* (2013.01); *A61M 5/31541* (2013.01); *A61M 5/48* (2013.01)

(56) References Cited

U.S. PATENT DOCUMENTS

| | | | | |
|---|---|---|---|---|
| 2003/0233070 | A1* | 12/2003 | De La Serna | F16K 17/30 604/141 |
| 2005/0015055 | A1* | 1/2005 | Yang | A61B 5/150236 604/199 |
| 2005/0165360 | A1* | 7/2005 | Stamp | A61M 5/2033 604/187 |
| 2007/0071829 | A1 | 3/2007 | Heger et al. | |
| 2008/0086079 | A1* | 4/2008 | Williamson | A61M 5/50 604/70 |
| 2009/0177158 | A1* | 7/2009 | Krumme | A61M 5/2053 604/143 |
| 2012/0071829 | A1 | 3/2012 | Edwards et al. | |
| 2014/0276898 | A1* | 9/2014 | Novak | A61F 2/148 606/107 |
| 2015/0190589 | A1* | 7/2015 | Bryant | A61M 5/46 604/117 |
| 2016/0243309 | A1* | 8/2016 | Cupicha | F16J 1/005 |

FOREIGN PATENT DOCUMENTS

| | | |
|---|---|---|
| CN | 1729028 | 2/2006 |
| CN | 1909939 | 2/2007 |
| CN | 101227943 | 7/2008 |
| EP | 2221076 | 8/2010 |
| WO | WO 2004/018023 | 3/2004 |
| WO | WO 2004/054645 | 7/2004 |
| WO | WO 2007/017052 | 2/2007 |

OTHER PUBLICATIONS

International Preliminary Report in International Application No. PCT/EP2016/060855, dated Nov. 14, 2017, 6 pages.

* cited by examiner

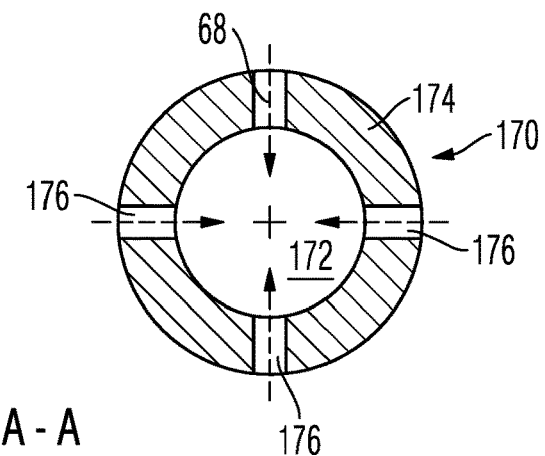
Fig. 9 A-A
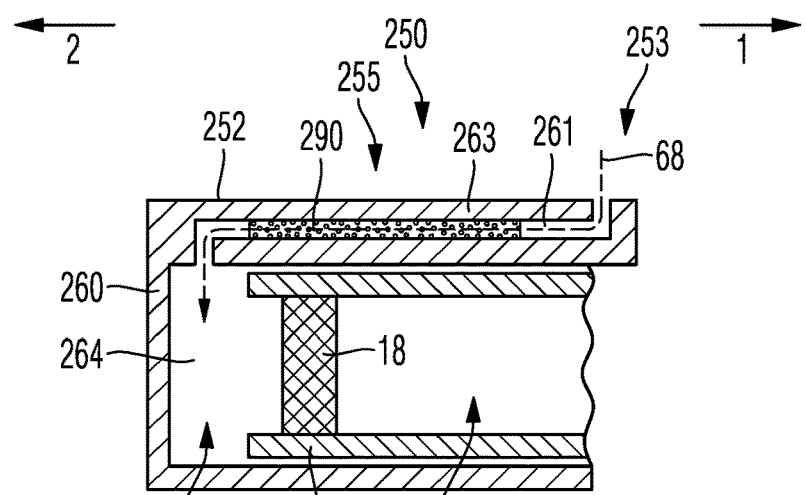
Fig. 10
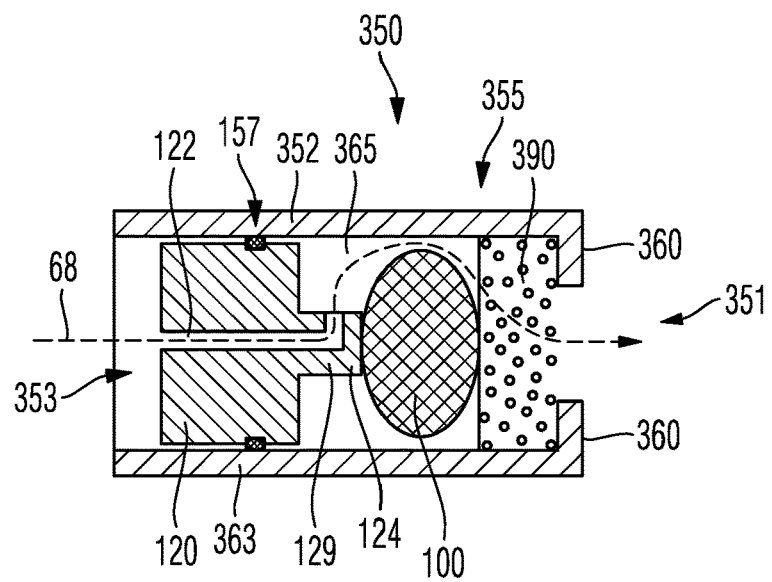
Fig. 11

INJECTION DEVICE FOR DELIVERY OF A LIQUID MEDICAMENT

CROSS REFERENCE TO RELATED APPLICATIONS

The present application is the national stage entry of International Patent Application No. PCT/EP2016/060855, filed on May 13, 2016, and claims priority to Application No. EP 15167539.4, filed on May 13, 2015, the disclosures of which are expressly incorporated herein in entirety by reference thereto.

TECHNICAL FIELD

The present disclosure relates to the field of injection devices and in particular to automatic injection devices for delivery of a liquid medicament by way of injection.

BACKGROUND

Automatic medicament delivery devices, such like autoinjectors provide a rather easy and convenient approach to inject a predefined dose of a liquid medicament into biological tissue. Such drug delivery devices may provide an injection needle extension and retraction mechanism in order to puncture biological tissue to which the liquid medicament is to be delivered. After the injection needle has been extended into an injection position drug delivery through the injection needle may automatically start. After termination of a delivery process the needle is typically retracted back into the housing. Since such drug delivery devices are intended for home- or self-medication their general handling should be easily understandable and unambiguous.

Additionally, such devices should provide a high degree of patient safety in order to avoid stitch damages or similar injuries. Depending on the therapy, the medication schedule as well as depending on the size of the dose of the liquid medicament to be injected, in some cases rather large injection volumes, e.g. larger than 1.25 ml and high viscosity of the liquid medicament may cause some difficulties and problems with existing drug delivery device designs. For instance, the total time for the delivery of the medicament may be out of a predefined range. Moreover, the viscosity and the total volume of the liquid medicament could lead to patient discomfort.

When such drug delivery or injection devices are of portable or mobile type they are typically equipped with some kind of energy storage to conduct a dispensing procedure and optionally to displace and to retract the injection needle. Document US 2012/0071829 A1 describes an apparatus featuring a medicament injector moveably disposed within a housing and an energy storage member configured to produce a force to move the medicament injector to an injection position in which a portion of a needle is disposed outside of a distal end portion of the housing.

The energy storage member is a compressed gas cylinder that is operable to produce a force that acts upon the medicament container to move the same between a first position and a second position. In response to a force produced by the pressurized gas, a moveable member and the medicament injector are moved towards a distal end portion of the housing, thereby exposing the needle from the housing. Thereafter a movable member continues to move a medicament container distally within a carrier. This continued movement of the medicament container places the needle in fluid communication with the medicament container, thereby allowing the medicament to be injected. Finally, the force from the pressurized gas causes the movable member to move within the medicament container, thereby expelling the medicament through the needle.

With such injection devices the amount of pressurized gas provided in a pressure container and the pressure level must be chosen to match with frictional forces that arise during the deployment of the device and during a dispensing action, i.e. as the piston is driven in a distal direction inside the barrel of a cartridge. Moreover, also the viscosity of the medicament to be dispensed and expelled may have an impact on the choice of a suitable pressure- or energy source. Depending on the size of a cartridge and the progress of an injection procedure the pressure level inside a pressure container may continuously decrease which may have a negative impact on the flow rate as well as on the general functionality or operability of the injection device. In order to overcome this deficiency one could think of increasing the size of the pressure container thereby simultaneously increasing the total amount of a pressurized fluid. But such a solution would be rather unattractive in terms of a miniaturization of the delivery device, which should be designed and configured for mobile applications or which should be carried along by the user or patient.

SUMMARY

Certain aspects of the subject matter of the present disclosure can be implemented to provide an improved pressure source or an improved way of handling a pressurized medium for pressure-driven or pressure-propelled injection devices. The solution should be particularly suitable for miniaturized injection devices that are intended to be carried along by the patient over a comparatively long time interval. Hence, the disclosure should provide a rather space-saving but long-lasting source of energy for pressure-driven injection devices. In addition, the solution should be easy to manufacture with a high degree of reproducibility at moderate or low costs. In addition, the injection device should be storable in a configuration ready to use. Hence, the injection device should be initially equipped with a medicament to be dispensed without any negative or shortening impact on the shelf life of the medicament.

In a first aspect an injection device for dispensing of a liquid medicament is provided. The device comprises an elongated housing extending in an axial direction to accommodate a cartridge. The cartridge is typically of tubular shape but is not limited to such a shape. The axial length or axial extension of the interior of the housing exceeds the axial length or axial extension of the cartridge. In this way, the cartridge is axially displaceable inside the housing between an undeployed proximal position and a deployed distal position. In the distal position the cartridge is in a configuration to expel a medicament contained therein whereas in the undeployed proximal position the cartridge rests in a storage position in which it is completely sealed to the surrounding. Typically, in the distal deployed position the cartridge is in fluid communication with an injection needle, or at least with a punctured fluid guiding structure, typically piercing a seal located at a distal end of the cartridge. Hence, the cartridge, in particular a distal seal thereof is pierceable to obtain access to the interior of the cartridge. This is typically obtained by displacing the cartridge from the undeployed proximal position towards the deployed distal position inside the housing, thereby pushing the cartridge with its distally located seal onto a tipped end of a hollow needle assembly, such like a cannula being fixed to the housing of the injection device.

In addition to the elongated housing the injection device further comprises a drive member axially displaceable inside the housing and being in sealed engagement with a sidewall of the housing. Typically, the drive member is operably engageable with the barrel of the cartridge, in particular with a proximal end of the cartridge's barrel. The drive member typically adapts the shape of the cross section of the interior of the elongated housing. The housing as well as the cartridge may be of tubular shape and extend parallel to each other. The drive member is typically slidably displaceable inside the housing. Simply by introducing a pressurized fluid from a proximal side into the housing pushes the drive member in distal direction relative to the housing and towards the cartridge, thereby pushing the cartridge from its proximal undeployed position into its deployed distal position.

The drive member has an abutment face to axially abut with a proximal end of a barrel of the cartridge. The abutment phase typically faces in distal direction to axially abut with the proximally facing end of the barrel of the cartridge. In this way and by pushing the drive member in distal direction the drive member is operable to displace the cartridge also distally, hence from the undeployed position towards the deployed position.

Furthermore, the drive member has an outlet located distally from the sealed engagement and further has an inlet located proximally from the sealed engagement of the drive member and the housing. The sealed engagement of drive member and the sidewall of the housing virtually divides the drive member into a distal portion and a proximal portion. The distal portion of the drive member comprises the outlet whereas the opposite proximal portion of the drive member comprises the inlet. The inlet and the outlet are in flow connection or flow communication with each other via a flow path. The flow path extends through the drive member, hence from the inlet towards the distally outlet. Typically, the inlet is located at a proximal side of the drive member whereas the outlet is located at a proximal side of the outlet.

At least one flow restrictor is arranged across or in this flow path. In this way, a fluid or gas pressure applied to the proximal side of the drive member may push and urge the drive member in distal direction to displace the cartridge from the undeployed proximal position to the deployed distal position with a comparatively high pressure. In a subsequent step and as the cartridge has reached its deployed distal position, in which it is typically in axial abutment with a distal end of the housing, thereby being axially and distally constrained with regard to the housing, the outlet of the drive member will be in flow connection or flow communication with a piston of the cartridge, which piston being slidably arranged inside the barrel of the cartridge.

Due to the flow restrictor inside the drive member the pressure of a pressurized medium, such like a pressurized fluid or gas emanating from the outlet of the drive member, is lower than the initial pressure applied to the inlet of the drive member. In this way the drive member serves not only as a component to axially displace the cartridge from the undeployed towards the deployed position but also provides a well-defined pressure drop. The drive member therefore has a double function. In a first aspect it serves to displace the entire cartridge from the undeployed proximal position to the deployed distal position by directly applying a distally directed thrust to the proximal end of the cartridge's barrel. In this function the drive member serves and acts like a piston rod or plunger exerting a distally directed driving force to the barrel of the cartridge.

In a second aspect the drive member provides a flow restrictor by way of which an input pressure can be reduced to a desired pressure level to smoothly and constantly displace the cartridge's piston in distal direction during a medicament dispensing procedure. Due to the drive member and its flow restrictor the input pressure to drive the injection process can be rather large. Hence, by means of the flow restrictor it is possible to increase the pressure level inside a pressure container, thereby increasing the energy density of such a pressure container.

This enables dispensing of rather large volumes of a liquid medicament without a substantial drop or decrease of the flow rate of the medicament in the progress of the injection procedure. Due to a comparatively high degree of pressure inside such a pressure container, the pressure of the pressurized medium emanating from the pressure container can be kept almost constant over the entire dispensing or injection procedure. Due to the implementation of the flow restrictor into the drive member a rather space saving and miniaturized solution is provided.

According to another embodiment the drive member comprises a body and a sealing member. The sealing member extends around the outer circumference of the body and is further in sealing engagement with the inside of the sidewall of the housing. The sealing member may comprise an O-ring extending around the tubular outer circumference of the body. For a well-defined attachment and fixing of the sealing member to the body it is conceivable, that the body comprises a circumferential groove to receive the sealing member. The outer circumference, hence the outer diameter of the body is slightly smaller than the inner diameter of the housing. The difference in diameters is smaller than the thickness of the ring of the sealing member multiplied by two. In other word, the difference of the inner radius of the housing and of the outer radius of the body is smaller than the radial extension of a cross sectional portion of the sealing member.

It is generally conceivable, that the body comprises a series of sealing members that are axially separated on the outer circumference of the body. Alternatively or additionally it is also conceivable, that the inside of the sidewall of the housing is equipped with at least one sealing member or with a sealing surface. Typically, the sealing member or a comparative sealing surface is made of an elastomeric sealing material, such like synthetic or natural rubber.

By means of the sealing member the drive member is in permanent sealing engagement with the sidewall of the housing. If the pressure level on a proximal side of the drive member is larger than on a distal side, the drive member will move to establish a pressure equilibrium. In this case the drive member will be driven in distal direction so as to decrease the pressure on the proximal side. Also when applying a negative pressure the drive member will always slide or move in the direction of the lower pressure level. By means of the at least one sealing member a permanent sealed engagement of drive member and sidewall of the housing can be established, thereby providing a pressure controllable axial displacement of the drive member inside the housing.

According to another embodiment the body comprises a receptacle delimited or confined in distal direction by a bottom or by an inwardly extending flange portion. Typically, the receptacle is open towards the proximal direction so as to receive a pressurized fluid or gas. By means of a bottom structure, typically extending perpendicular to the axial elongation of the housing or the drive member an abutment or support structure for the flow restrictor can be provided. The inwardly extending flange portion may particularly serve to axially support a support member acting as a support for the flow restrictor. The flange portion may extend radially inwardly from the sidewall of the housing. If the receptacle of the body is delimited by a bottom, it is of particular benefit when the bottom is provided with a through opening or aperture being in fluid connection with the outlet of the drive member or even forming the drive member's outlet. The receptacle of the body serves to accommodate the flow restrictor in a well-defined, precise and reproducible way. The surface of the bottom or flange portion may further provide a well-defined and optionally an even-shaped support structure for the flow restrictor.

According to another embodiment the body comprises a sidewall with a threaded section, typically on the inside. Typically, this threaded section of the sidewall is provided near a proximal end of the body, e.g. opposite the bottom or the flange portion, forming or delimiting the distal end of the receptacle. By means of the threaded section a clamping member may be inserted and may be axially displaceable inside the receptacle in a well-defined way.

According to a further embodiment the injection device comprises a clamping member axially displaceably arranged inside the receptacle of the body of the drive member. The clamping member further has an axial through opening, typically forming a part of the flow path for the pressurized fluid or gas. The clamping member typically serves to fix or to clamp the flow restrictor inside the receptacle of the body of the drive member. Typically, the clamping member comprises a distally facing distal surface to apply a distally directed pressure towards and onto the flow restrictor being mechanically supported by the flange portion or the bottom of the receptacle.

According to another embodiment the clamping member comprises a threaded section, typically an outer threaded section threadedly engaged with the threaded section of the sidewall of the body. In this way clamping member and body can be axially displaced simply by screwing the clamping member into or out of the sidewall of the body. The clamping member may be configured or may comprise a grub screw having a hollow interior so as to provide at least a portion of the flow path through the drive member. Typically, a distally facing surface of the clamping member is substantially even or flat-shaped so as to exert a spatially homogeneous pressure onto the flow restrictor sandwiched between the clamping member and the bottom or flange portion of the receptacle.

By means of mutually corresponding threaded sections of the clamping member and the sidewall of the receptacle of the drive member a clamping force as well as an axial tension emanating from the clamping member can be arbitrarily modified. Especially for squeezable flow restrictors the flow resistance of the flow restrictor could be arbitrarily modified and configured simply by rotating or screwing the clamping member relative to the body.

According to another embodiment the flow restrictor comprises at least one porous restriction member. The restriction member comprises a porous structure with a mean pore size in the region of a few micrometers or sub-micrometers. Typically, the mean pore size as well as the specific geometric dimensions and the geometric shape of the restriction member is adapted and configured to the viscosity of the pressurized fluid or gas flowing along the flow path of the drive member. Use of porous media for the restriction member is advantageous in that said porous media exhibit a well-defined flow resistance. Furthermore, porous materials to form the restriction member are commercially available at moderate costs. In addition, these materials typically require only limited space inside the drive member.

In effect, porous media to form the restriction member provide excellent reproducibility and in terms of pressure drop. Moreover, such materials show excellent long term stability.

According to a further embodiment the porous restriction member is axially sandwiched between the clamping member and a support member axially constrained inside the body. The support member serves to mechanically stabilize the porous restriction member. The support member may comprise a grid of a comparatively stiff material. Alternatively, the support member may comprise a rather rigid and stiff disc to provide mechanical stability to the flow restrictor. Keeping the flow restrictor in a predefined shape might be of crucial importance to counteract any local pressure-induced deformations of the porous restriction member, which could otherwise have an impact on the pore size of the restriction member. Given that the restriction member extends across an orifice or aperture in the bottom or the flange portion of the receptacle of the body it is generally conceivable that the porous restriction member is subject to a bending so that the restriction member would form a bulged portion. In such bended or bulged regions, the average pore size may deviate from the pore size in the surrounding un-deformed restriction member. In order to counteract a conceivable deformation the support member provides mechanical stability to the porous restriction member.

According to a further embodiment the porous restriction member is axially sandwiched between the bottom of a cup-shaped insert and a distally-facing surface of a punch element arranged inside the insert. The dimensions and geometry of the punch element, in particular its outer geometry exactly match with the interior geometry of the cup-shaped insert. The restriction member and optionally also the support member are sandwiched between the bottom of the insert and the distally-facing surface of the punch element. Since the porous restriction member is located on the bottom of the insert and since almost the complete interior space of the insert is filled or occupied by the punch element the outer circumference of the restriction member is effectively sealed.

Typically, the insert as well as the punch member both comprise a bore or a through opening forming part of and constituting the flow path extending through the drive member. The insert, the punch element and at least the porous restriction member, optionally also the support member sandwiched between the punch element and the insert form a kind of a preassembly that is arranged inside the receptacle of the body of the drive member and which is finally subject to axial compression as the clamping member is inserted into the receptacle from the proximal direction. Hence, the insert, the restriction member, the support member and the punch element are axially sandwiched between the bottom or flange portion of the receptacle of the body and the clamping member threadedly engaged with the sidewall of the receptacle.

According to another embodiment the porous restriction member comprises a thermoplastic membrane filter material, a sintered filter material or a foamed material. All of these materials are commercially available for filter applications. Porous restriction members made of these materials are producible with high precision and provide a well-defined pressure drop per unit volume. The thermoplastic membrane filter material may comprise a fabric of polyester, polyamide, or polypropylene or combinations thereof. Alternatively, a thermoplastic membrane filter material may comprise a fleece of one of the above mentioned thermoplastic polymers. The membrane, fabric or fleece may further comprise materials such like silver, polycarbonate, polyester, polysulfone or polyethersulfone cellulose, hydrophilic or hydrophobic PVDF-membranes-nylon or acrylic copolymer materials and mixtures thereof. In a typical embodiment the filter material comprises a polycarbonate track-etched membrane with pore sizes ranging from 0.01 μm to 0.05 μm. The actual thickness of the membrane filter of disc shape may range between 2 μm to 10 μm or 15 μm. In a typical embodiment the thickness of the polycarbonate-track-etched membrane is around 6 μm.

When implemented as a sintered filter material the porous restriction member typically comprises pore sizes larger than 0.5 μm. In comparison to thermal plastic membrane filters sintered filter membranes have to be thicker or have to occupy more space in the flow path of the drive member. When making use of a foam or a foam material the porous restriction member may have pores with a median pore size in the region of even 5 μm or more. Since foam materials are typically compressible the pore size of the porous restriction member could be easily modified by way of compression.

Variable compression of the porous restriction member is attainable via axially displacing the clamping member relative to the receptacle of the drive member. Due to the threaded engagement of clamping member and the body of the drive member the porous restriction member is squeezable with variable pressure. An increase of the pressure acting on the porous restriction member leads to a reduction of the median pore size thereof. As a consequence, the flow resistance of the restriction member increases and the pressure drop obtainable by the flow restrictor increases accordingly. In this way the pressure drop provided by the at least one flow restrictor of the drive member can be arbitrarily adapted and the flow restrictor is tunable or adjustable to a predefined degree.

According to another embodiment the support member extends across and aperture of the body. It is either permeable to a fluid flow or to a gas flow flowing along the flow path of the drive member. Alternatively, if support member it is impermeable to the fluid or gas its outer circumference forms a radial gap to the inside of the sidewall of the body. The gap may be of annular shape. Alternatively, several radial gaps are formed that are separated in circumferential direction by radially outwardly extending studs. Furthermore, the disc-shaped support member may also comprises at least one or several axial through openings along its periphery. Hence, the support member may comprise radially inwardly extending recesses along its outer circumference, wherein each recess forms a radial gap to the inside of the sidewall of the body.

The radial gap formed between the support member and the inside of the sidewall of the body forms a flow restricting aperture inherently increasing the flow resistance of the drive member in a well-defined way.

Making use of an impermeable support member allows making use of rather stable and rigid materials for the support member. It is conceivable, that the support member comprises a closed structure of a thermoplastic material. The support member could also be made of a metallic material or a metal alloy.

In a further embodiment the injection device also comprises a needle assembly attachable to a distal end of the housing. The needle assembly comprises a tipped needle extending axially into the housing with a proximal end. The needle may be of cannula type. Typically, its proximal end is tipped and the needle is hollow so as to puncture a distally located seal of the cartridge in order to gain access to the interior of the cartridge for the purpose of dispensing of the medicament. Typically, the needle assembly is detachable to the distal end of the housing. For this the housing and the needle assembly comprise mutually corresponding fastening elements, such like mutually corresponding threads or mutually corresponding snap connectors.

The needle may comprise a double-tipped injection needle, wherein both opposite ends, a proximal end as well as a distal end are tapered or tipped. When implemented as a double-tipped injection needle the distal end of the needle is configured to penetrate biological tissue to deliver the liquid medicament into said tissue. Otherwise and when implemented as a single tipped needle with the tipped end facing in proximal direction the opposite distal end may be connectable to a tubing or the like fluid guiding assembly.

The injection device further comprises a closure sealing the proximal end of the housing and having a pressure connection to introduce a pressurized fluid or gas into the housing. The closure is typically formed by an end cap matching with the geometry and cross section of the housing's proximal end. The cartridge is located axially between the end cap and the needle assembly. In the undeployed proximal position the cartridge is located remote to the needle assembly. Since the end cap seals the proximal end of the housing and since the drive member as well as the cartridge are located distally to the end cap introducing of a pressurized medium into the housing from a proximal side leads to a pressure buildup between the end cap and the drive member, which due to the sealed engagement with the sidewall of the housing experiences a distally directed sliding motion, thereby pushing the cartridge in distal direction towards the needle assembly.

At least one of the needle assembly or a distal end of the housing comprises a stop feature to limit the distally directed displacement of the cartridge. In this way either the housing itself or the needle assembly defines the deployed distal position of the cartridge. When a cartridge abuts with a respective distal stop feature, e.g. with a radially inwardly extending flange-like distal end of the housing, its proximal seal, typically implemented as a pierceable septum is actually pierced by the proximally extending tipped end of the needle. As long as the injection device is not used the cartridge is typically fixed in the undeployed proximal position. It is hence disconnected from the needle assembly. The shelf life of the injection device is therefore equivalent or identical to the inherent shelf life of the cartridge.

For instance, the cartridge may be frictionally fixed inside the housing, e.g. by means of an O-ring extending around the outer circumference of the cartridge and along the inside of the housing's sidewall. The size and the material of such an O-ring is selected such, that the cartridge is inhibited and hindered from a self-acting displacement inside the housing. The frictional engagement of the cartridge and the housing is substantially larger than the gravitational force acting on the cartridge. The frictional engagement of cartridge and housing is also substantially smaller than the driving force emanating from the drive member as soon as a source of a pressurized medium is connected to the pressure connection. In this way a distally directed displacement of the cartridge to arrive in the deployed distal position can be obtained exclusively by way of connecting the pressure connection with a source of energy, in particular with a pressure container or pressure reservoir.

It is generally conceivable, that at least one of the proximal end cap and the needle assembly is detachable from the housing. In this way the injection device allows and enables a replacement of an empty cartridge. The injection device is therefore implementable as a reusable device. Since the injection device is particularly configured to store an unused cartridge therein for a comparatively long time interval the injection device may be also configured and implemented as a disposable device. Then the cartridge readily arranged inside the housing of the injection device is not replaceable. The needle assembly as well as the end cap are permanently and undetachably connected to the housing of the injection device. A brute force disconnection of either needle assembly or end cap from the housing would then lead to an at least partial destruction of the housing, the needle assembly or the end cap thereby rendering the injection device unusable. Such a disposable device could directly serve as an anti-counterfeiting means.

According to another embodiment a cartridge is assembled in the housing in the undeployed position. In the undeployed position the cartridge is typically in axial abutment with the drive member. In this way a pressure-induced distally directed displacement of the drive member is directly transferred to a respective distally directed displacement of the cartridge. Otherwise, if the drive member and the cartridge would be initially assembled inside the housing with an axial gap therebetween distally directed displacement of the drive member would initially lead to a collision with the proximal end of the barrel of the cartridge. This could harm the integrity of the cartridge and eventually lead to fracture of the cartridge. By arranging the proximal end of the barrel of the cartridge in direct abutment with the drive member in an initial undeployed configuration of the injection device a risk of a collision-induced fracture of the cartridge can be effectively reduced.

According to another embodiment the outlet of the drive member, hence the distal end of the flow path extending through the drive member is in flow connection with a proximally facing thrust receiving surface of a piston axially displaceably arranged inside the barrel of the cartridge. While the drive member is subject to the pressure level of the pressurized fluid or gas entering the housing of the injection device the outlet of the drive member only provides a reduced pressure level which is then applicable to the piston of the cartridge. While the drive member due to its axial abutment with the proximal end of the barrel of the cartridge serves to displace the cartridge directly into the deployed distal position a further flow of the pressurized fluid is only present to the cartridge, hence to its piston at a reduced level. In this way the integration of the flow restrictor into the drive member provides a two-fold functionality. Initially and as the pressurized fluid or gas enters the housing at a comparatively high pressure level the cartridge is abruptly displaced in distal direction to arrive in the deployed distal position. Thereafter and since the cartridge is in axial abutment with a distal stop feature of either the housing or the needle assembly a reduced pressure emanating from the outlet of the flow restrictor of the drive member is present to the piston of the cartridge, thereby displacing the piston relative to the cartridge in a well-defined and pressure reduced manner.

In the present context, the distal direction points in the direction of the dispensing and of the device, where, preferably a needle assembly is provided having a double-tipped injection needle that is to be inserted into biological tissue or into the skin of a patient for delivery of the medicament. The proximal end or proximal direction denotes the end of the device or a component thereof, which is furthest away from the dispensing end.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivatives are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39), des Pro36 [Met(O)14 Trp(O2)25, Asp28] Exendin-4(1-39), des Pro36 [Met(O)14 Trp(O2)25, IsoAsp28] Exendin-4(1-39); or des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(02)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(02)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, K or A, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present disclosure without departing from the spirit and scope of the disclosure. Further, it is to be noted, that any reference numerals used in the appended claims are not to be construed as limiting the scope of the disclosure.

BRIEF DESCRIPTION OF THE FIGURES

In the following, embodiments of the drive mechanism and the injection device are described in detail by making reference to the drawings, in which:

FIG. 9 shows a cross section along A-A of FIG. 8, FIG. 10 shows a part of a longitudinal cross section of another embodiment of the drive member, FIG. 11 shows a further embodiment of the drive member.

DETAILED DESCRIPTION

Figure 1:
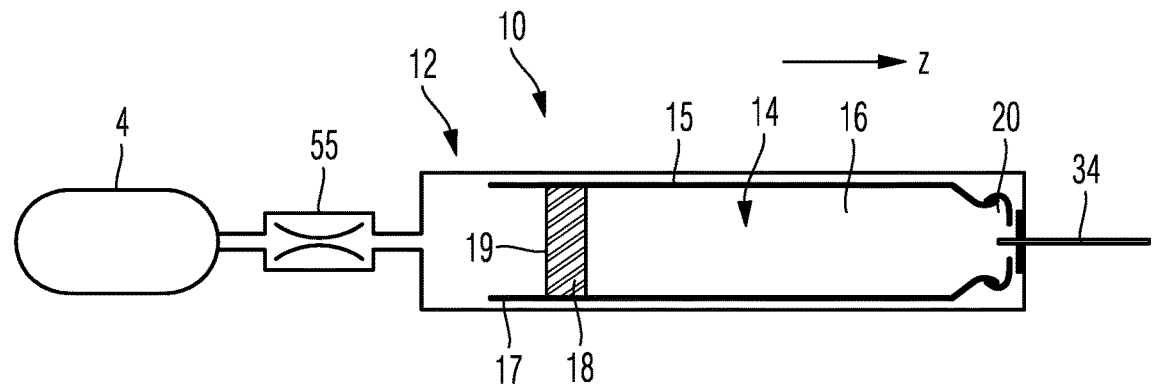
FIG. 1 schematically shows the injection device in combination with a pressure container and a flow restrictor.

In FIGS. 1-4 the injection device 10 is schematically illustrated. It comprises a housing 12, typically of tubular shape extending in an axial direction (z). Inside the housing 12 there is arranged a cartridge 14 comprising a tubular barrel 15 and being filled with a liquid medicament 16. Near its distal end 22 the housing 12 is provided with a needle assembly 30 having a cup-shaped needle hub 32 and an injection needle 34 extending in longitudinal or axial direction (z). In distal direction 1 the injection needle faces away from the injection device 10. With its distal end the injection needle 34 may penetrate or pierce biological tissue to deliver the liquid medicament 16. With its opposite proximal end 38 facing in proximal direction the injection needle 34 is configured to penetrate and to puncture a seal 20 at the distal end of the cartridge 14. The proximal end extends in proximal direction through an aperture 24 of the distal end 22 of the housing 12.

In the proximal direction 2, hence near a proximal end 17 the cartridge 14 is sealed by a piston 18 acting as a displaceable seal of the cartridge 14. The piston 18, typically of elastomeric material, such like a natural or synthetic rubber is displaceable in distal direction 1 in order to expel a predefined amount of the medicament 16 via the injection needle 34, typically at a predefined flow rate. The piston 18 comprises a proximally-facing thrust receiving surface 19, which is subject to an increased pressure level. With the present injection device 10 a pressurized medium, such like a pressurized fluid or gas enters the proximal side of the housing 12 to apply a driving pressure to the piston 18.

For this the housing 12 is in fluid connection or fluid communication with a pressure container 4 providing a medium, typically in form of a pressurized gas. In order to control the velocity of displacement of the piston 18 and to control the flow rate of the medicament 16 through the injection needle 34 there is further provided a flow restrictor 55 as schematically illustrated in FIG. 1. The flow restrictor 55 is located in the flow path 68 between the pressure container 4 and the piston 18. In the various embodiments according to the present disclosure as shown in FIGS. 1-11 the injection device 10 comprises a drive member 50, 150, 250, 350 located inside the housing 12 proximally to the cartridge 14. The drive member 50, 150, 250, 350 is in sealed engagement 57 with the inside of the sidewall 13 of the housing 12.

Figure 2:
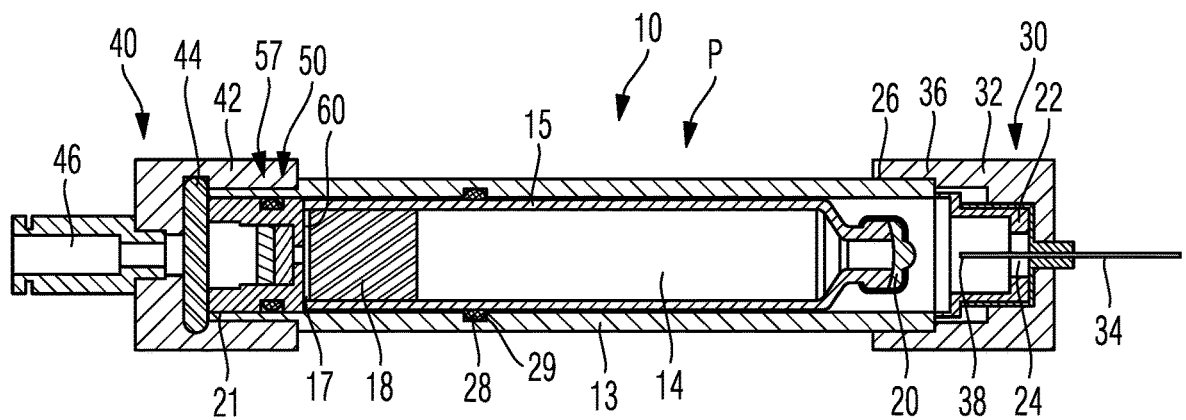
FIG. 2 shows a longitudinal cross section through the injection device with the cartridge in undeployed proximal position.
Figure 3:
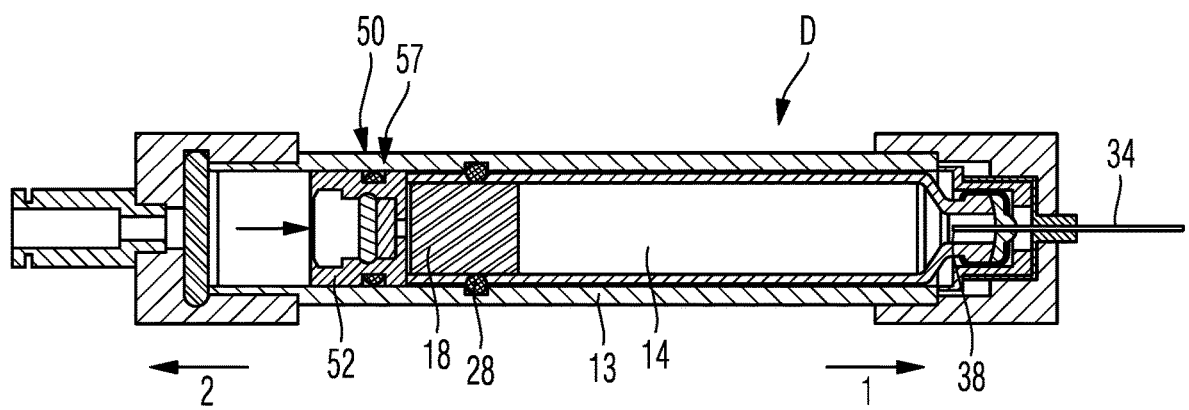
FIG. 3 shows the injection device according to FIG. 2 with the cartridge in deployed distal position.
Figure 4:
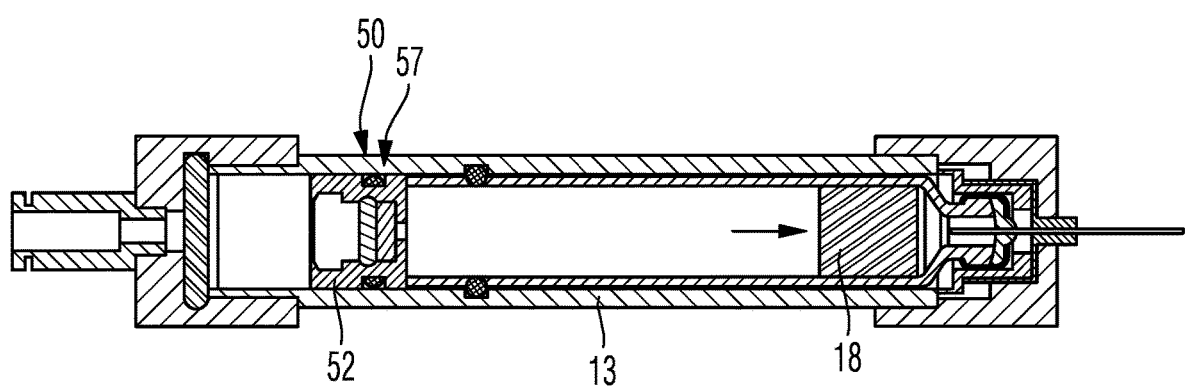
FIG. 4 shows the injection device according to FIGS. 2 and 3 at the end of a dispensing procedure.

The drive member 50, 150, 250, 350 has transverse dimensions, hence perpendicular to the axial direction (z) that match with the transverse dimensions of the proximal end 17 of the barrel 15 of the cartridge 14. In this way the drive member 50 is operable to displace the cartridge 14 from an undeployed proximal position P as shown in FIG. 2 towards and into a deployed distal position D as shown in FIGS. 3 and 4. For this the proximal end 21 of the housing 12 is sealed by a closure 40. The closure 40 comprises an end cap 42 in sealed engagement with the proximal end of the tubular-shaped housing 12. As shown in FIG. 2-4 there is provided a seal 44, typically in form of a sealing disc, between the proximal end 21 of the housing 12 and the bottom face of the end cap 42. The end cap 42, hence the closure 40 is further provided with a pressure connection 46. The pressure connection 46 typically comprises a standardized connector in order to releasably couple the closure 40 and hence the housing 12 of the injection device 10 with an energy source in form of a pressure container 4.

As shown in FIGS. 2-4 the cartridge 14 is in frictional engagement with the housing 12 by means of at least one O-ring 28. This O-ring 28 extends around the outer circumference of the tubular-shaped barrel 15 of the cartridge 14. The O-ring 28 is located in a circumferential recess 29 of the inside of the sidewall 13 of the housing 12. Due to the frictional engagement between the housing 12 and the cartridge 14 the cartridge 14 is securely fixable in the undeployed proximal position P as long as no substantial pressure is provided via the pressure connection 46.

However, as soon as a pressure is applied to the interior of the housing 12 as indicated in FIG. 3 the cartridge 14 is immediately subject to a distally directed displacement until its distal end gets in axial abutment with the radially inwardly extending flange-like distal end 22 of the housing 12. Alternatively, it is conceivable, that the needle assembly 30 provides a respective distal stop for the cartridge 14. Typically, the needle assembly 30 comprises fastening elements 36 to releasably engage with correspondingly-shaped fastening elements 26 on the outer circumference of the housing 12. Mutually corresponding fastening elements 26, 36 may be configured as mutually corresponding threaded structures or snap-fit elements.

The drive member 50, 150, 250, 350 as shown in more detail in FIGS. 5-11 acts and behaves like a plunger in direct mechanical engagement with the barrel 15 of the cartridge 14. As it is apparent in an initial configuration according to FIG. 2 a distally facing abutment face 60 of the drive member 50 is in direct axial abutment with the proximal end 17 of the barrel 15 of the cartridge 14. As soon as the pressurized fluid or gas enters the proximal end of the housing 12 the drive member 50 is subject to a distally directed displacement thereby pushing the cartridge 14 in distal direction 1 towards the deployed distal position D as shown in FIG. 3.

Figure 5:
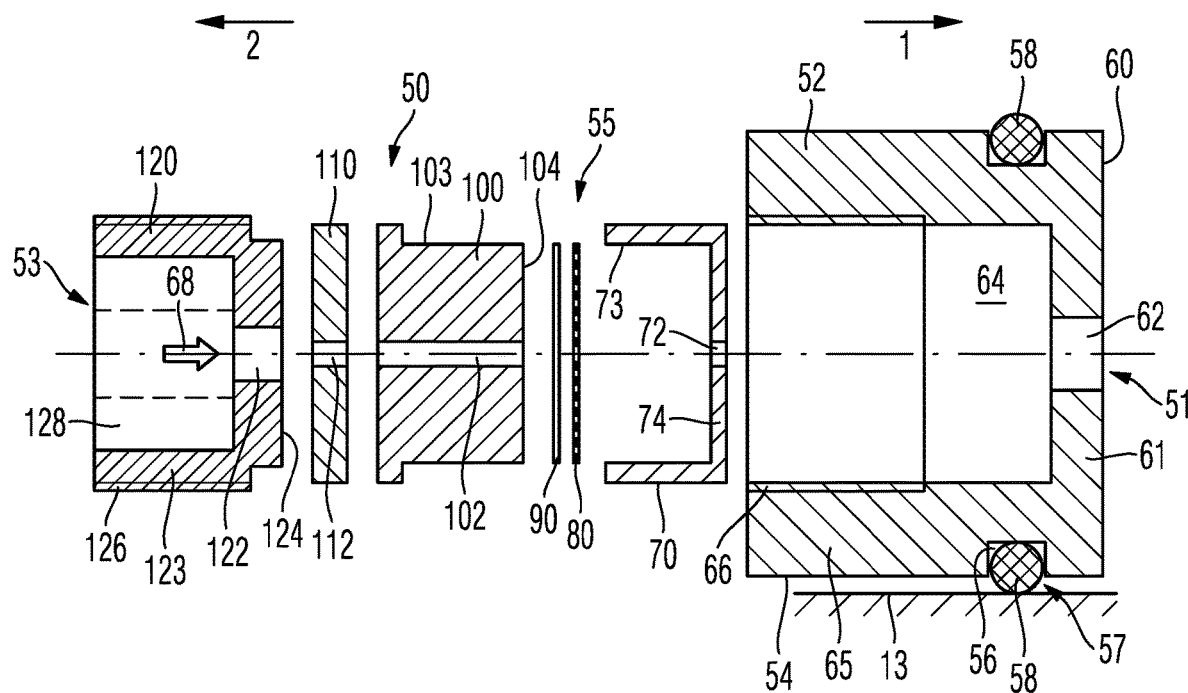
FIG. 5 shows a cross section of one embodiment of the drive member in an exploded configuration.

In order to act as a pressure-driven driving element the drive member 50, 150, 250, 350 is in sealed engagement 57 with the housing 12, in particular with the inside of the sidewall 13 of the housing 12. As shown in FIG. 5, the drive member 50 comprises a body 52 of cylindrical or tubular shape having an outer circumference 54 that substantially matches with the interior cross section of the housing 12. Between the outer circumference 54 of the body 50 and inside of the sidewall 13 of the housing 12 there is provided an annular sealing member 58 to provide the sealed engagement of drive member 50 and housing 12. As soon as a pressure is applied proximal to the sealed engagement 57 established between the drive member 50 and the sidewall 13 of the housing 12 the drive member 50 and its body 52 is immediately subject to a distally directed sliding displacement relative to the housing 12. For fixing the sealing member 58 to the body 52 of the drive member 50 the body 52 comprises an annular recess 56 in the outer circumference 54 of the body 52 in which the annular sealing member 58, typically in form of an O-ring, is located.

Figure 6:
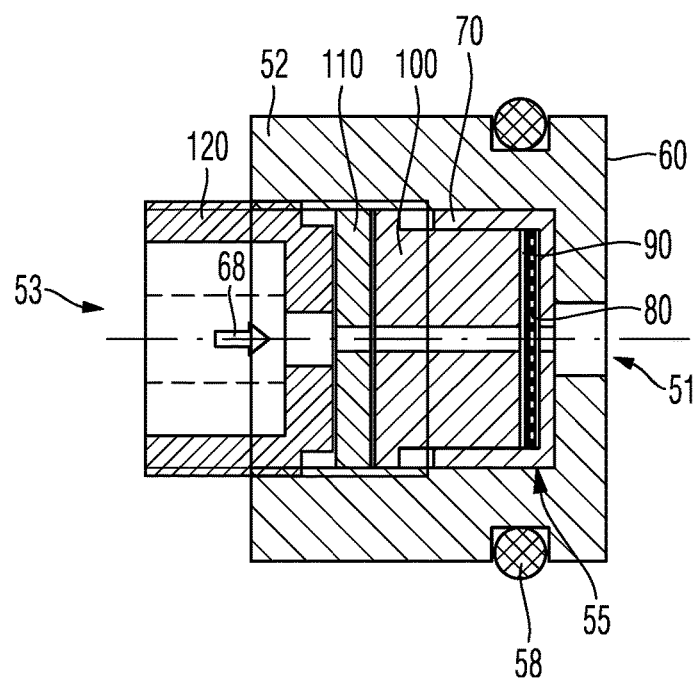
FIG. 6 shows the drive member according to FIG. 5 in the assembled configuration.

The drive member 50 as shown in FIGS. 5 and 6 comprises a flow restrictor 55 across or in a flow path 68 extending from an inlet 53 towards an outlet 51 of the drive member 50. The drive member 50 is permeable to the pressurized fluid or gas present to its proximal end. But the flow path 68 and the flow restrictor 55 provide a well-defined pressure drop. Hence, the pressurized medium entering the inlet 53 at a comparatively high pressure level leaves the distally directed outlet 51 of the drive member 50 at a reduced pressure level. The outlet 51 is in flow connection or flow communication with the proximally-facing thrust receiving surface 19 of the piston 18 of the cartridge 14. In this way it is possible to make use of a comparatively high pressurized medium inside the pressure container 4 while simultaneously providing only a reduced and well-defined pressure level to the piston 18 of the cartridge 14.

In this way, use of comparatively highly pressurized media inside the pressure container 4 is possible so that an eventual drop of a pressure level during an injection procedure is substantially insignificant. The body 52 of the drive member 50 is of cup-shape and comprises a bottom 61 featuring a distally-facing planar shaped abutment face 60. Centrally located inside the bottom 61 there is provided an aperture 62 acting as the outlet 51 of the drive member 50. The cup-shaped and sleeve-like body 52 comprises a receptacle 64 formed by a tubular-shaped sidewall 65.

As shown in FIG. 5, a proximal section of the inside of the sidewall 65 is a threaded section 66 to threadedly engage with a correspondingly threaded section 126 of a clamping member 120. The receptacle 64 is configured to receive a cup-shaped insert 70 having a planar-shaped bottom 74 facing in distal direction. In an assembly configuration as shown in FIG. 6 the bottom 74 of the insert 70 is in direct axial abutment with an inside facing portion of the bottom 61 of the body 52. Also the insert 70 comprises a centrally located aperture 72, which overlaps with the aperture 62 of the body 52. Both apertures 72, 62 contribute and belong to the flow path 68 for the pressurized fluid. The insert 70 serves to accommodate a support member 80 as well as a porous restriction member 90. The support member 80 may comprise a permeable grid, a woven, a fabric or a fleece to mechanically support the porous restriction member 90. The porous restriction member 90 may comprise a thermoplastic membrane filter material as described above.

In the embodiment of FIGS. 5 and 6 both the porous restriction member 90 as well as the support member 80 are of disc-like shape. The porous restriction member 90 as well as the support member 80 may be bonded along their outer circumference. Typically, the outer dimensions of the porous restriction member 90 and the support member 80 precisely match with the inside geometry of the cup-shaped insert 70. The support member 80 serves to provide mechanical stability and rigidity to the porous restriction member, in particular in the area across the aperture 72 of the insert 70 and hence across the aperture 62 of the body 52. Otherwise, the porous restriction member 90 could be subject to local deformation or dilatation, thus changing its pore size and hence its flow resistance.

Proximally from the porous restriction member 90 there is provided a punch element 100 having an aperture 102, typically configured as an axially extending bore. The punch element 100 comprises a planar-shaped distal surface 104 and serves to squeeze the assembly of support member 80 and porous restriction member 90 inside the insert. Typically, the inside of the sidewall 73 of the insert 70 exactly matches with the outer circumference 103 of the punch element 100. When the punch element 100 is inserted into the insert 70 the outer circumference 103 and the inside of the sidewall 73 are in a sealed engagement.

Alternatively and instead of insert 70 and punch element 100 it is also conceivable to keep the assembly of support member 80 and porous restriction member 90 inside the receptacle 64 by means of at least one or several O-rings or comparable annular sealing members.

There is further provided and intermediate disc 110 also comprising a centrally located aperture 112. The intermediate disc 110 serves as a mechanical protection for the distal end face of the punch element 100. Finally and proximal to the intermediate disc 110 there is provided a clamping member 120 also having a planar-shaped distally-facing bottom 124 to axially abut with the proximal face of the intermediate disc 110. In the assembled configuration the intermediate disc 110 is axially sandwiched between the punch element 100 and the clamping member 120. As further shown in FIG. 6, the hollow clamping member 120 not only comprises a centrally located aperture 122 but also has an interior 128 formed by a sidewall 123. The interior 128 of the sidewall or the inside of the sidewall 123 may comprise a wrench flat to engage with a correspondingly shaped spanner or wrench.

The clamping member 120 comprises a threaded section 126 along its outer circumference to threadedly engage with the threaded section 66 of the body 52 of the drive member 50. In this way and by screwing the clamping member 120 into the receptacle 64 of the body 52 the assembly of intermediate disc 110, punch element 100, porous restriction member 90, support member 80 and insert 70 can be squeezed in axial direction to a well-defined or predefined degree so as to provide a tight and gas proof engagement of the aforementioned components of the flow restrictor 55. In order to provide sufficient and high clamping forces the body 52 and the clamping member 120 may comprise a metallic material. For instance, the body 52 can be made of aluminum whereas the clamping member 120 can be made of aluminum or steel. The punch element 100 as well as the intermediate disc 110 are typically made of a rather rigid plastic material, such like polyoxymethylene (POM).

The porous restriction member 90, typically in form of a filter membrane is made of polycarbonate whereas the support member 80 can be a fleece. The support member 80 may comprise or consists of polyamid, polyester, polypropylen, cotton or combinations thereof. The support member 80 prevents that the porous restriction member 90 rips when it is subject to a substantial fluid pressure. The medium pore size of the support member 80 is at least 5 to 15 times larger than the medium pore size of the porous restriction member 90. Typically, the medium pore size of the support member 80 is at least 10 times larger than the medium pore size of the porous restriction member 90.

The porous restriction member 90 can be implemented as a track membrane. Good results were actually obtained with a medium pore size in a range between 0.03 µm to 0.2 µm. In particular embodiments a medium pore size of 0.05 µm was implemented. The membrane of the porous restriction member may comprise or consist of polycarbonate.

The apertures 122, 112, 102, 72 and 62 of the various components 120, 110, 100, 70, 52 are all inline. Hence they flush in axial direction (z). In this way a flow restriction or a throttle function is mainly provided by the assembly of the porous restriction member 90 and the support member 80.

Figure 7:
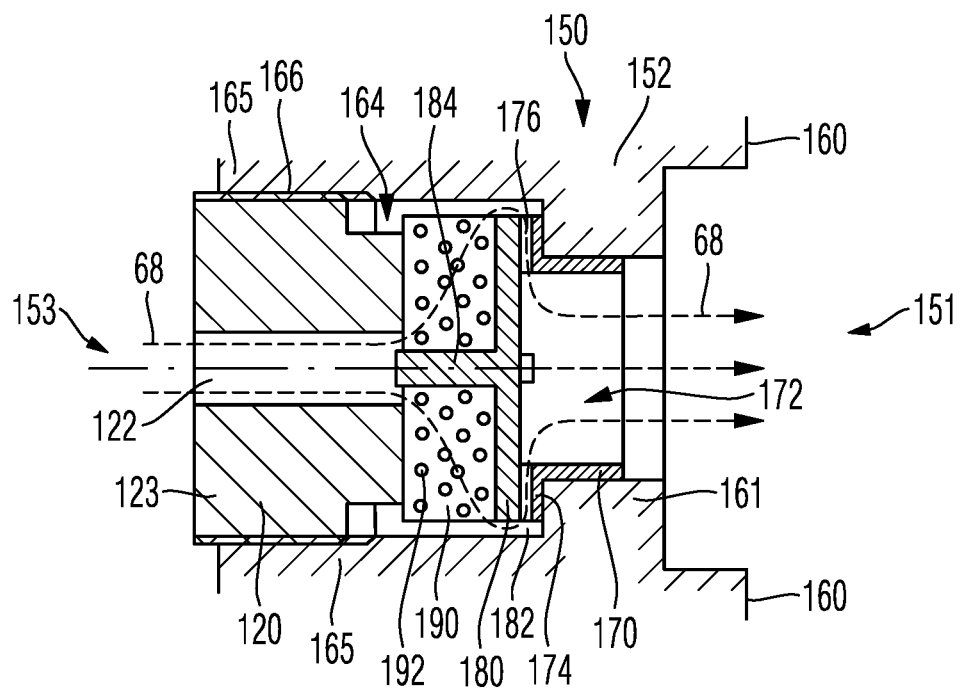
FIG. 7 shows an alternative embodiment of a drive member with a rather uncompressed porous restriction member.
Figure 8:
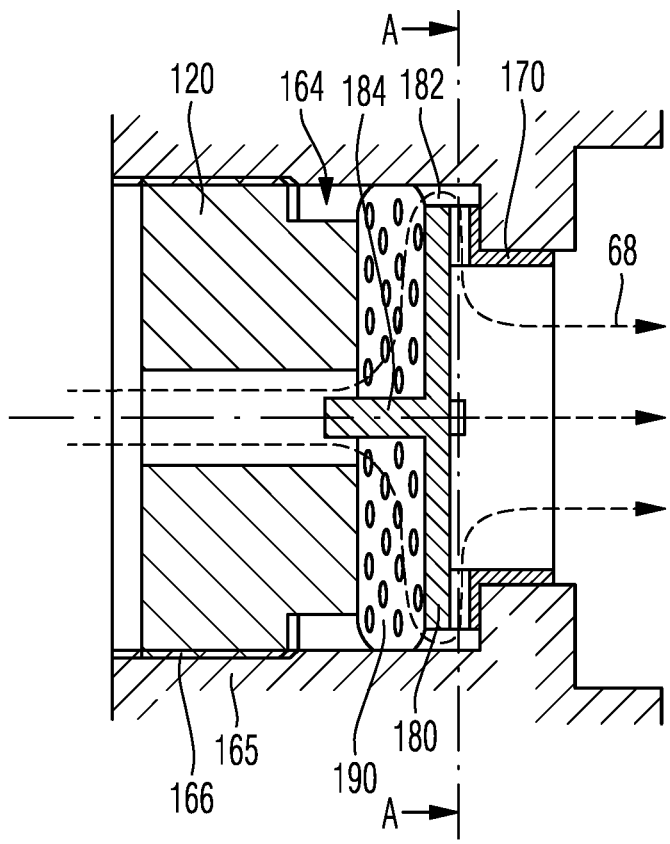
FIG. 8 shows the drive member according to FIG. 7 with a compressed porous restriction member.

In the alternative embodiment as shown in FIGS. 7-9 identical or like components as in the embodiment according to FIGS. 5 and 6 are denoted with equal or like reference numbers, typically increased by the number 100. There, the drive member 150 comprises a body 152 of a slightly different geometry. Instead of a substantially closed bottom 61 the body 152 comprises a radially inwardly extending flange portion 161 to provide axial abutment for an insert 170 comprising a radially outwardly extending flange portion 174. The insert 170 is of substantially tubular shape and comprises a sidewall 173 that is confined by the radially inwardly-facing sidewall portion 163 of the stepped down flange portion 161 of the sidewall 165 of the body 150.

The radially outwardly extending flange portion 174 is provided with numerous radially extending grooves 176 facing in proximal direction 2. The body 160 also comprises a distally-facing abutment face 160 to axially engage with the proximal end 17 of the barrel 15 of the cartridge 14. The aperture 172 of the insert 170 forms or contributes to the outlet 151 of the flow restrictor 155. Likewise the embodiment as described in FIGS. 5 and 6 the body 152 according to FIGS. 7-9 also comprises a receptacle 164 with a threaded section 166 at its proximal end of its sidewall 165. The threaded section 166 is threadedly engageable with the clamping member 120 as already explained in connection with the embodiment according to FIGS. 5 and 6.

Proximal to the insert 170 there is provided a T-shaped support member 180. The support member 180 is impermeable to the pressurized fluid or pressurized gas but provides mechanical support to the porous restriction member 190. Contrary to the embodiment as shown in FIGS. 5 and 6 the porous restriction member 190 is comparatively thick in axial direction. It may comprise a foamed material. From a comparison of FIGS. 7 and 8 it is apparent that the porous restriction member 190 is elastic and is hence squeezable to a certain degree by screwing the clamping member 120 further into the receptacle 164 of the body 152. As a consequence, the shape and/or the overall size of the pores 192 of the porous restriction member 1090 changes or decreases, thereby increasing the flow resistance of the porous restriction member 90.

Furthermore since the support member 180 is impermeable to the pressurized fluid or gas there is provided a radial gap 182 at least in sections along the outer circumference of the support member 180 and the inside of the sidewall 165 of the body 152. The flow path 68 is illustrated in FIGS. 7 and 8. Due to the radial gap or due to several radial gaps 182 the pressurized fluid arriving through the centrally located bore or aperture 122 radially centrally enters the porous restriction member 190 and is redirected radially outwardly through the porous restriction member 190 to flow through the radial gap 182 and through the radially inwardly extending grooves 176 of the flange portion 174 of the insert 170 before the fluid enters the aperture 172 and hence the outlet 151 of the insert 170 and the drive member 150, respectively, at a reduced pressure level.

As it is illustrated in FIGS. 7 and 8 the porous restriction member 190 is axially intersected by a radially centrally located tapped 184 of the support member 180. The tappet 184 extends axially in proximal direction 2 and may act as a mechanical bearing for the disc shaped support member 180. By means of the tapped 184 the disc shaped support 180 member can be radially fixed by the restriction member 190, which is typically in radial abutment with the inside of the sidewall 165 of the body 152. Likewise the embodiment of FIGS. 5 and 6 also the alternative embodiment of the drive member 150 according to FIGS. 7-9 comprises an inlet 153 formed by a hollow portion of a wrench flat on the inside of a sidewall 123 of the clamping member.

In the further alternative embodiments according to FIGS. 10 and 11 only a portion of the cross section of the drive members 250, 350 and their bodies 252, 352 is illustrated. Also there, similar or like components are indicated with like or identical reference numbers, increased by 100 or 200, respectively. The drive member 250 as shown in FIG. 10 comprises an inlet 253 in fluid communication with a channel structure 261 extending in a sidewall 263 of a body 255 being axially displaceable inside the housing 12 of the injection device 10. The channel structure 251 is rather elongated and is provided with a longitudinally extending porous restriction member 290. In this embodiment the porous restriction member 290 may comprise a sintered structure or a sintered filter material typically having a pore size that is substantially larger than the median pore size of a membrane filter material. As shown in FIG. 10 the channel structure 251 is in fluid communication with an outlet 251 which is located inside a cup-shaped receptacle 264 on a distal side of the body 252.

As indicated in FIG. 10 at least a proximal portion, hence a proximal end 17 of the barrel 15 of the cartridge 14 is located inside this receptacle 264, which is open towards the distal direction 1. Here, the bottom of the receptacle 264 form the abutment face 260 to axially abut with the proximal end 17 of the barrel 15 of the cartridge 14. In this way the body 252 and the cartridge 14 can be mechanically engaged so that any distally-directed displacement of the body 252 equally and unalterably transfers into a corresponding distally-directed displacement of the cartridge 14.

In the further embodiment according to FIG. 11 the drive member 350 also comprises a body 352 in which a clamping member 120 is axially slidably arranged. Hence, the body 352 comprises a receptacle 365 formed by a tubular-shaped sidewall 363. With a distal abutment face 360 the body 352 is axially engagable with the barrel 15 of the cartridge 14. A distally facing bottom 124 of the clamping member 120 is in axial abutment with a flexible punch element 100 inside the receptacle 365. As shown in FIG. 11 the punch element 100 is of somewhat ellipsoidal, oval or spherical shape. It is in direct abutment with a central portion of a proximally-facing surface of a porous restriction member 390. Also here the porous restriction member 390 may be supported by a support member to provide sufficient mechanical stability and/or rigidity. Distal to the porous restriction member 390 there is located the outlet 351 of the drive member 350. The proximal end of the receptacle 365 of the body 352 forms or constitutes the inlet 353 of the drive member 350.

The flow path 68 extends through the aperture 122 of the clamping member 100. However, the aperture 122 or the channel formed by the aperture 122 is somewhat bended or L-shaped. It exits to a lateral side face of a distally-facing axial projection 129 of the clamping member 120, which is in direct abutment with the elastically deformable punch element 100. There may be some axially extending recesses in the inside face of the sidewall 363 of the body 352 to form a bypass channel for the pressurized fluid or gas. The punched element 100 is typically impermeable to the pressurized gas or fluid and covers only a portion of the porous restriction member 390. As a comparatively large pressure is present to the proximal surface of the clamping member 120 the punch element 100 is further squeezed in axial direction.

As a consequence, its contact surface with the porous restriction member 390 enlarges so that the effective surface of the restriction member 390 that is subject to a fluid or gas pressure is effectively reduced. In this way a dynamic and automatically regulating flow restrictor 355 is provided. The porous restriction member 390 might be compressible or substantially incompressible. In combination with the elastically deformable punch element 100 the portion of the proximal surface of the porous restriction member 390 being subject to a fluid or gas penetration can be regulated. The clamping member 120 according to FIG. 11 is in sealed engagement 157 with the sidewall 363 of the body 352. By flexibly deforming the punch element 100 the cross section of the porous restriction member 390 subject to a fluid-or-gas flow is modified.

Figure 12:
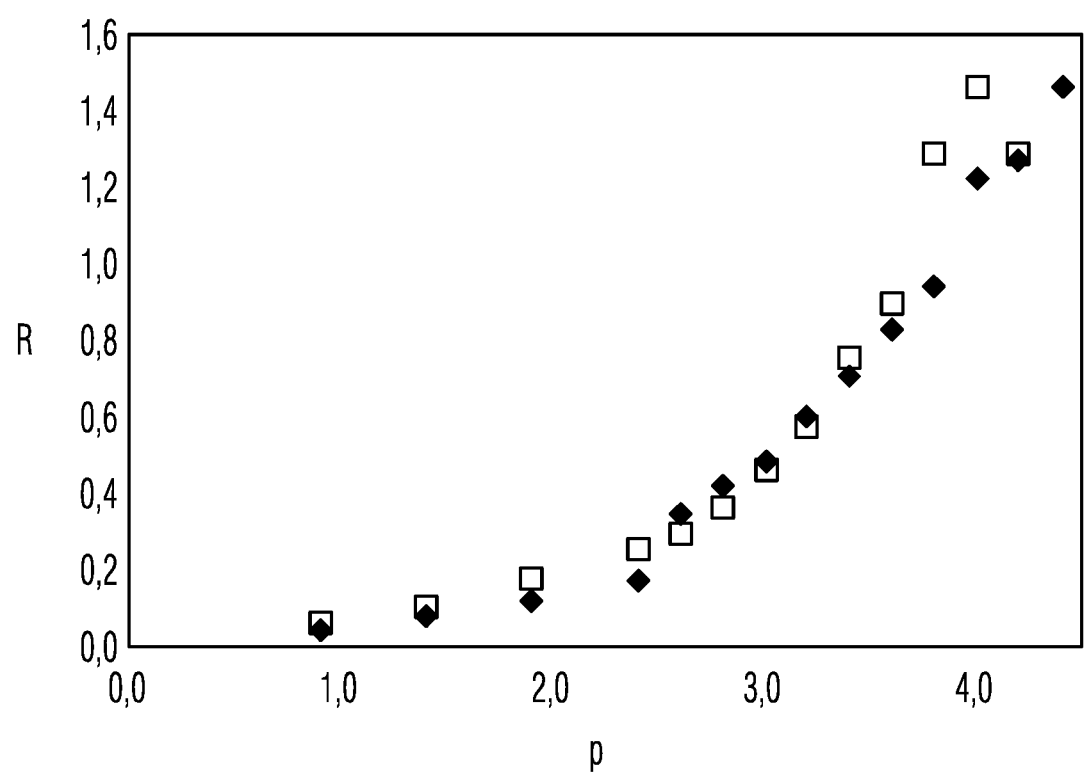
FIG. 12 shows a diagram of a flow rate versus a pressure across the drive member.

In FIG. 12 a diagram is illustrated showing a flow rate R in liters per minute per square centimeter versus a pressure difference p measured in bar across the drive member 50, hence between the inlet 53 and the outlet 51. The rhombic measurement points relate to a measurement series with constantly increasing pressure difference while the quadratic measurement points reflect the measured flow rate with a decreasing pressure difference when starting with a maximum pressure difference of about 4 bar. As can be seen from FIG. 12, the flow rate R is in a non-linear relation to the pressure difference. There is almost no hysteresis between a measurement with rising or decreasing pressure. The diagram therefore indicated a high degree of reproducibility of the flow restrictors 55, 155, 255, 355.

LIST OF REFERENCE NUMBERS 1 distal direction
2 proximal direction
4 pressure container
10 injection device
12 housing
13 sidewall
14 cartridge
15 barrel
16 medicament
17 proximal end
18 piston
19 thrust receiving surface
20 seal
21 proximal end
22 distal end
24 aperture
26 fastening element
28 O-ring
29 recess
30 needle assembly
32 needle hub
34 injection needle
36 fastening element
38 proximal end
40 closure
42 end cap
44 seal
46 connection
50 drive member
51 outlet
52 body 53 inlet
54 outer circumference
55 flow restrictor
56 groove
57 sealed engagement
58 sealing member
60 abutment face
61 bottom
62 aperture
64 receptacle
65 sidewall
66 threaded section
68 flow path
70 insert
72 aperture
73 sidewall
74 bottom
80 support member
90 porous restriction member
100 punch element
102 aperture
103 outer circumference
104 distal surface
110 intermediate disc
112 aperture
120 clamping member
122 aperture
123 sidewall
124 bottom
126 threaded section
128 interior
129 projection
150 drive member
151 outlet
152 body
153 inlet
155 flow restrictor
157 sealed engagement
160 abutment face
161 flange portion
163 sidewall portion
164 receptacle
165 sidewall
170 insert
172 aperture
173 sidewall
174 flange portion
176 groove
180 support member
182 radial gap
184 tappet
190 porous restriction member
192 pore
250 drive member
251 outlet
252 body
253 inlet
255 flow restrictor
260 abutment face
261 channel structure
263 sidewall
264 receptacle
290 porous restriction member
350 drive member
351 outlet
352 body
353 inlet
355 flow restrictor
360 abutment face
363 sidewall
365 receptacle
390 porous restriction member
P Proximal position
D Distal position

The invention claimed is:

1. An injection device for dispensing of a liquid medicament, the injection device comprising:
an elongated housing extending in an axial direction to accommodate a cartridge, wherein an axial length of an interior of the elongated housing exceeds an axial length of the cartridge to allow the cartridge to be axially displaced inside the elongated housing between an undeployed proximal position and a deployed distal position; and
a drive member axially displaceable inside the elongated housing and being in sealed engagement with a side wall of the elongated housing,
wherein the drive member has an abutment face to axially abut with a proximal end of a barrel of the cartridge to displace the cartridge from the undeployed proximal position towards the deployed distal position,
wherein the drive member has an outlet located distally from the sealed engagement and further has an inlet located proximally from the sealed engagement, the inlet and the outlet being axially displaceable inside the elongated housing,
wherein the inlet and the outlet are in flow connection with each other via a flow path extending through the drive member, the flow path being axially displaceable inside the elongated housing, and
wherein at least one flow restrictor is arranged across or in the flow path.

2. The injection device according to claim 1, wherein the drive member comprises a body and a sealing member, wherein the sealing member extends around an outer circumference of the body.

3. The injection device according to claim 2, wherein the body comprises a receptacle delimited in a distal direction by a bottom or by an inwardly extending flange portion.

4. The injection device according to claim 2, wherein the body comprises a sidewall with a threaded section.

5. The injection device according to claim 3, further comprising a clamping member axially displaceably arranged inside the receptacle and having an axial through opening.

6. The injection device according to claim 4, further comprising a clamping member having a threaded section threadedly engaged with the threaded section of the sidewall of the body.

7. The injection device according to claim 1, wherein the at least one flow restrictor comprises at least one porous restriction member.

8. The injection device according to claim 7, wherein the at least one porous restriction member is axially sandwiched between a clamping member and a support member axially constrained inside a body of the drive member.

9. The injection device according to claim 7, wherein the at least one porous restriction member is axially sandwiched between a bottom of a cup shaped insert and a distally facing surface of a punch element arranged inside the cup shaped insert.

10. The injection device according to claim 7, wherein the at least one porous restriction member comprises a thermoplastic membrane filter material, a sintered filter material or a foamed material.

11. The injection device according to claim 10, wherein the at least one porous restriction member is squeezable in the axial direction to modify its average pore size.

12. The injection device according to claim 8, wherein the support member extends across an aperture of the body and is either permeable to a fluid flow or gas flow or an outer circumference of the support member forms a radial gap to the inside of a sidewall of the body.

13. The injection device according to claim 1, further comprising:
- a needle assembly attachable to a distal end of the elongated housing, wherein the needle assembly comprises a tipped needle extending axially into the elongated housing with a proximal end, and
- a closure sealing the proximal end of the elongated housing and having a pressure connection to introduce a pressurized fluid or gas into the elongated housing.

14. The injection device according to claim 1, further comprising the cartridge assembled inside the elongated housing in the undeployed proximal position in axial abutment with the drive member.

15. The injection device according to claim 14, wherein the outlet of the drive member is in flow connection with a proximally facing thrust receiving surface of a piston axially displaceably arranged inside the barrel of the cartridge.

16. The injection device according to claim 14, wherein the cartridge comprises a medicament.

17. The injection device according to claim 16, wherein the medicament comprises a pharmaceutically active compound.

* * * * *